United States Patent
Li et al.

(10) Patent No.: US 6,409,878 B1
(45) Date of Patent: Jun. 25, 2002

(54) AUTOMATIC DECAPSULATION SYSTEM UTILIZING AN ACID RESISTANT, HIGH HEAT ENDURANCE AND FLEXIBLE SHEET COUPLED TO A RUBBER GASKET AND A METHOD OF USE

(75) Inventors: Xia Li, Fremont; Joseph Vu, San Jose; Mohammad Massoodi, Los Altos; Jose Hulog, San Jose, all of CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 54 days.

(21) Appl. No.: 09/680,558

(22) Filed: Oct. 5, 2000

Related U.S. Application Data

(63) Continuation-in-part of application No. 09/551,300, filed on Apr. 18, 2000.

(51) Int. Cl.$^7$ ................................................ C23F 1/02
(52) U.S. Cl. .................................................. 156/345.23
(58) Field of Search ................................... 156/345.23

(56) References Cited

U.S. PATENT DOCUMENTS

| | | | | |
|---|---|---|---|---|
| 4,826,556 A | * | 5/1989 | Kobayashi | 156/345 |
| 5,252,179 A | * | 10/1993 | Ellerson et al. | 156/655 |
| 5,443,675 A | * | 8/1995 | Wensink | 156/345 |
| 5,766,496 A | * | 6/1998 | Martin | 216/56 |
| 5,783,098 A | * | 7/1998 | Martin et al. | 216/56 |
| 5,792,305 A | * | 8/1998 | Winsemius et al. | 156/345 |
| 5,855,727 A | * | 1/1999 | Martin et al. | 156/345 |

* cited by examiner

*Primary Examiner*—Gregory Mills
*Assistant Examiner*—A. Michelle Crowell
(74) *Attorney, Agent, or Firm*—Sawyer Law Group LLP

(57) ABSTRACT

An automatic decapsulation system for a device is disclosed. The system comprises an etch plate, an etch head, an acid resistant, high heat endurance and flexible sheet coupled to the etch plate, and a rubber gasket disposed between the sheet and the etch head. The sheet provides a precise etch window and a self-aligning gasket for the device. The rubber gasket creates a tight seal between the device, the sheet, and the etch head. A system in accordance with the present invention utilizes an acid resistant, high heat endurance and flexible sheet in combination with a rubber gasket to seal the device for decapsulation and to provide a well-defined etch window. In addition, the sheet being utilized as the gasket is also utilized as the fixture, thereby eliminating the need to align the gasket to the metal fixture utilized in the conventional system.

19 Claims, 6 Drawing Sheets

AUTOMATIC DECAPSULATION SYSTEM UTILIZING AN ACID RESISTANT, HIGH HEAT ENDURANCE AND FLEXIBLE SHEET COUPLED TO A RUBBER GASKET AND A METHOD OF USE

CROSS-REFERENCE TO RELATED APPLICATION

This is a continuation-in-part of U.S. Patent application No. 09/551,300 filed on Apr. 18, 2000, entitled "Automatic Decapsulation System Utilizing An Acid Resistant, High Heat Endurance and Flexible Sheet and a Method of Use," which is herein incorporated by reference.

FIELD OF THE INVENTION

The present invention relates generally to automatic decapsulators and more particularly to the decapsulation gaskets utilized in such decapsulators.

BACKGROUND OF THE INVENTION

Automatic decapsulators are used to expose the die in any plastic package or device by an etching away the die's plastic covering. Either fuming sulfuric, fuming nitric, or mixed filming nitric and sulfuric acids may be used as an etchant. Decapsulation is a fast and safe process that produces a clean, uncorroded die surface. When fuming nitric acid is used as the etchant, there is little or no damage to the die surface or bond pads. Fuming sulfuric acid is normally used at an elevated temperature to remove the plastics that are not compatible with fuming nitric acid. The etching process is performed under pressure in an inert atmosphere to reduce metal oxidation and to reduce the production of harmful fumes.

FIG. 1a illustrates a side view of a typical system for automatic decapsulation of a device. The system 10 includes a safety cover 11 which is coupled to an etch plate 13. The system 10 also includes a positioning fixture 12 coupled to the etch plate 13 which is typically metal and is aligned with a package 16 and a gasket 14, typically made of rubber. The gasket 14 is positioned under the device 16 with an etch window in the gasket's center. The etchant is provided through the etch window to the device 16 via the etch head 18. Referring now to FIG. 1b, a top view of the conventional system is shown. As is seen, the fixture 12 and the gasket 14 must be aligned to etch the device 16 properly.

For many current plastic packages, such as plastic ball grid array (PBGA) or fine ball grid array (FBGA) packages, the plastic materials can only be removed using fuming sulfuric acid at a high temperature (>200° C.). The etch time can be very long (>500 seconds) for some large size packages. Serious problems can occur while decapsulating a PBGA or FBGA package. First, the rubber gasket, which provides the etch window and seals the device to the etch head, distorts slightly when the rubber gasket is compressed between the device and the etch head. As a result, the etchant can attack areas not intended to be etched. With large devices, this slight distortion is not a concern, however, with small FBGA packages (which can be as small as 5 mm×5 mm), the slight distortion in the etch window causes over etching, which in turn leads to an accumulation of etching acid at the package edges. This accumulation can wreck havoc because the back side of a PBGA or FBGA package generally contains a printed circuit board ("PCB") substrate and solder ball connections. The excess acid at the package edge can creep to the backside of the package, ruining the PCB substrate and solder ball connections on the package.

Second, because the device sits directly on the rubber gasket, which is usually soaked with etching acid during decapsulation, the PCB substrate of the package can corrode. Finally, because the decapsulation temperature exceeds the melting point of the solder balls on the backside of the package, the solder balls can be smashed by the protection plate, which rests on the backside of the package. For the reasons discussed above, conventional decapsulation systems utilizing a rubber gasket are not feasible for PBGA and small FBGA packages. What is needed is a system and method to overcome the above-identified problems.

SUMMARY OF THE INVENTION

An automatic decapsulation system for a device is disclosed. The system comprises an etch plate, an etch head, an acid resistant and high heat endurance sheet, and a rubber gasket disposed between the etch head and the acid resistant and high heat endurance sheet. The sheet and rubber gasket combination provide a tight seal between the device and the etch head, and a precise etch window that does not deform during decapsulation. Moreover, the sheet automatically aligns the etch window with the device, thereby reducing the amount of time taken to otherwise align the gasket. In a preferred embodiment of the present invention, the system includes a device securing unit to secure the device without damaging the backside of the package.

A system in accordance with the present invention utilizes an acid resistant and high heat endurance sheet coupled with a rubber gasket to seal the device for decapsulation and to provide a well-defined etch window. In addition, the sheet/rubber gasket combination is also utilized as the fixture, thereby eliminating the need to align the gasket to the metal fixture utilized in the conventional system.

DETAILED DESCRIPTION

The present invention relates generally to automatic decapsulators and more particularly to the decapsulation gaskets utilized in such decapsulators. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Figure 1A:
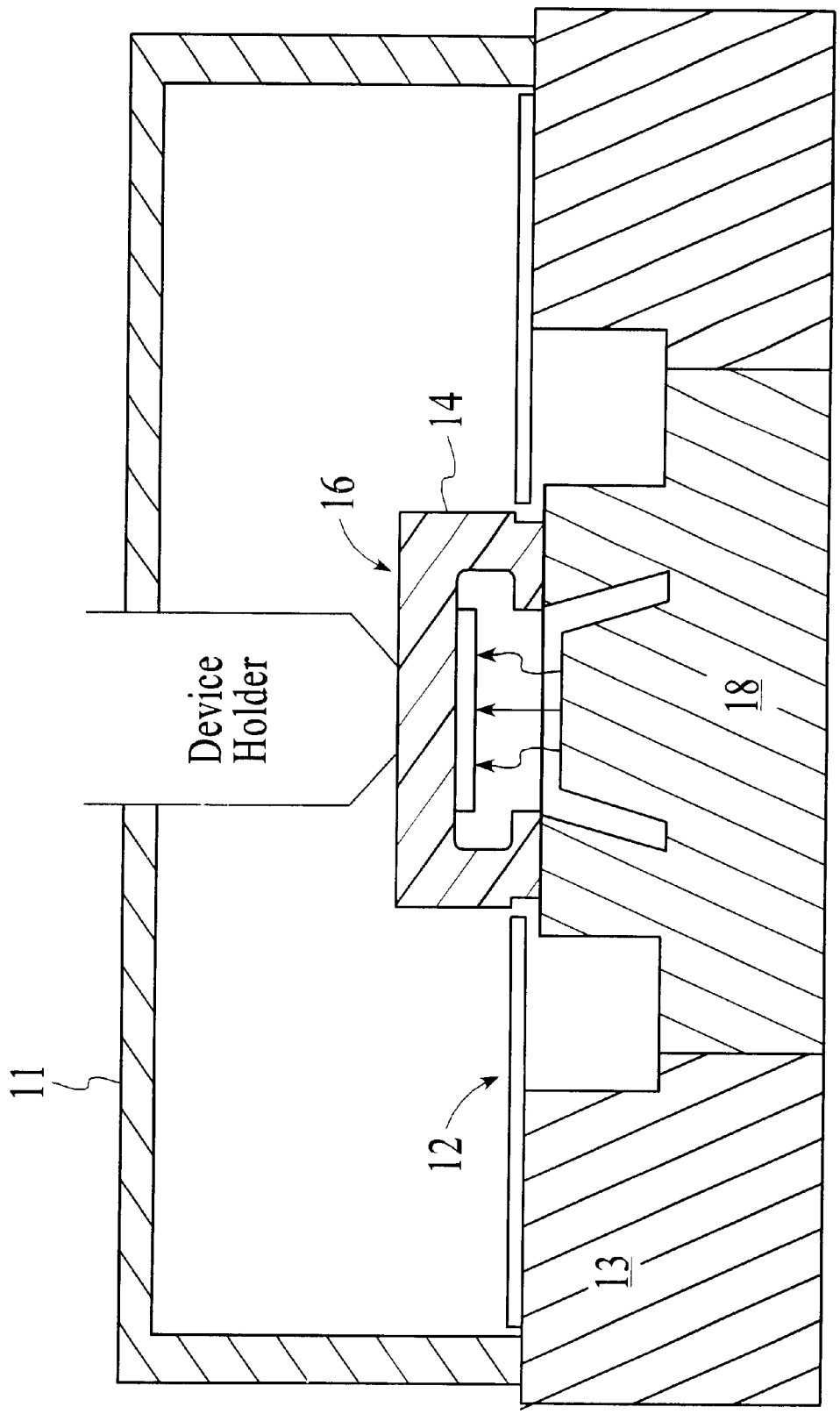
FIG. 1a illustrates a side view of a conventional system for autodecapsulation.

FIG. 1a illustrates a typical system for automatic decapsulation of a device. The system 10 includes a rubber gasket 14, which is positioned between the device 16 and the etch head 18. An opening in the center of the rubber gasket 14 serves as an etch window for controlling the areas on the device 16 that are to be exposed to the etchant. During decapsulation, the device 16 presses down upon the rubber gasket 14, creating a tight seal with the etch head 18. The etchant is then provided by the etch head 18 through the etch window to the device 16.

Because the rubber gasket 14 is compressible, its etch window deforms slightly when the gasket 14 is pressed between the device 16 and etch head 18. Although this slight deformation is inconsequential when etching large devices, one of ordinary skill in the art will recognize that it can cause extensive damage to small FBGA or PBGA packages. In particular, the deformed etch window can cause over etching of the FBGA or PBGA package, which can eventually damage the components on the backside of the package, as discussed above. Moreover, because FBGA and PBGA decapsulation is performed at high acid temperature (>200 C.) and sometimes for long etch time periods, the rubber gasket 14 tends to deteriorate rapidly. Thus, debris from the rubber gasket 14 can contaminate the device 16 and clog the etch head 18. What is needed is a system and method to overcome the above-identified problems.

Co-pending U.S. patent application Ser. No. 09/551,300 entitled "Automatic Decapsulation System Utilizing An Acid Resistant, High Heat Endurance And Flexible Sheet And Method Of Use" filed on Apr. 18, 2000, discloses utilizing a sheet of material which has acid resistance, high heat endurance and flexibility, rather than a rubber gasket to seal the device for decapsulation. The sheet of metal is preferably made of TEFLON® (polyfluoroletraethylene ("PFTE")).

Figures 1B, 2B:
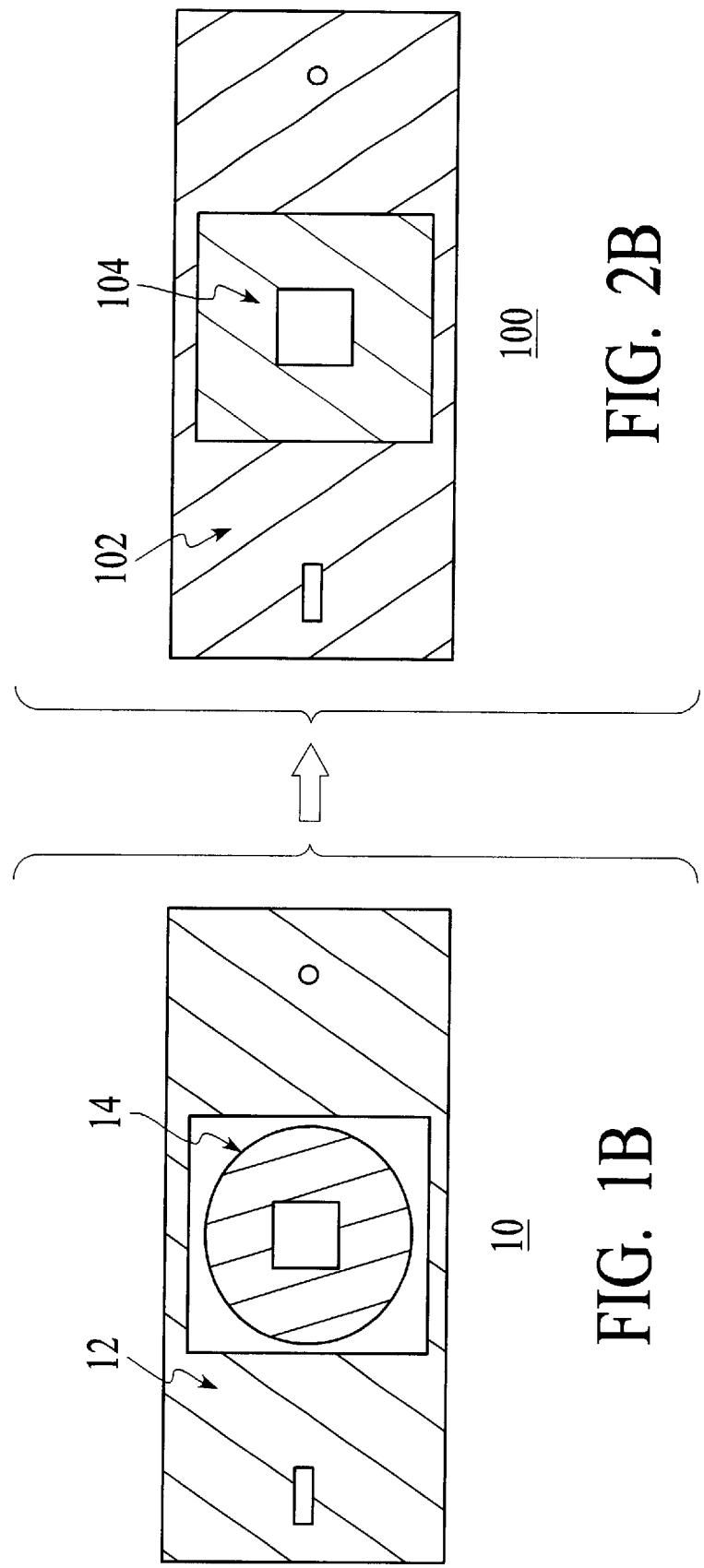
FIG. 1b is a top view of the conventional decapsulation system.
FIG. 2b illustrates a top view of the decapsulation system in accordance with the co-pending application.
Figure 2A:
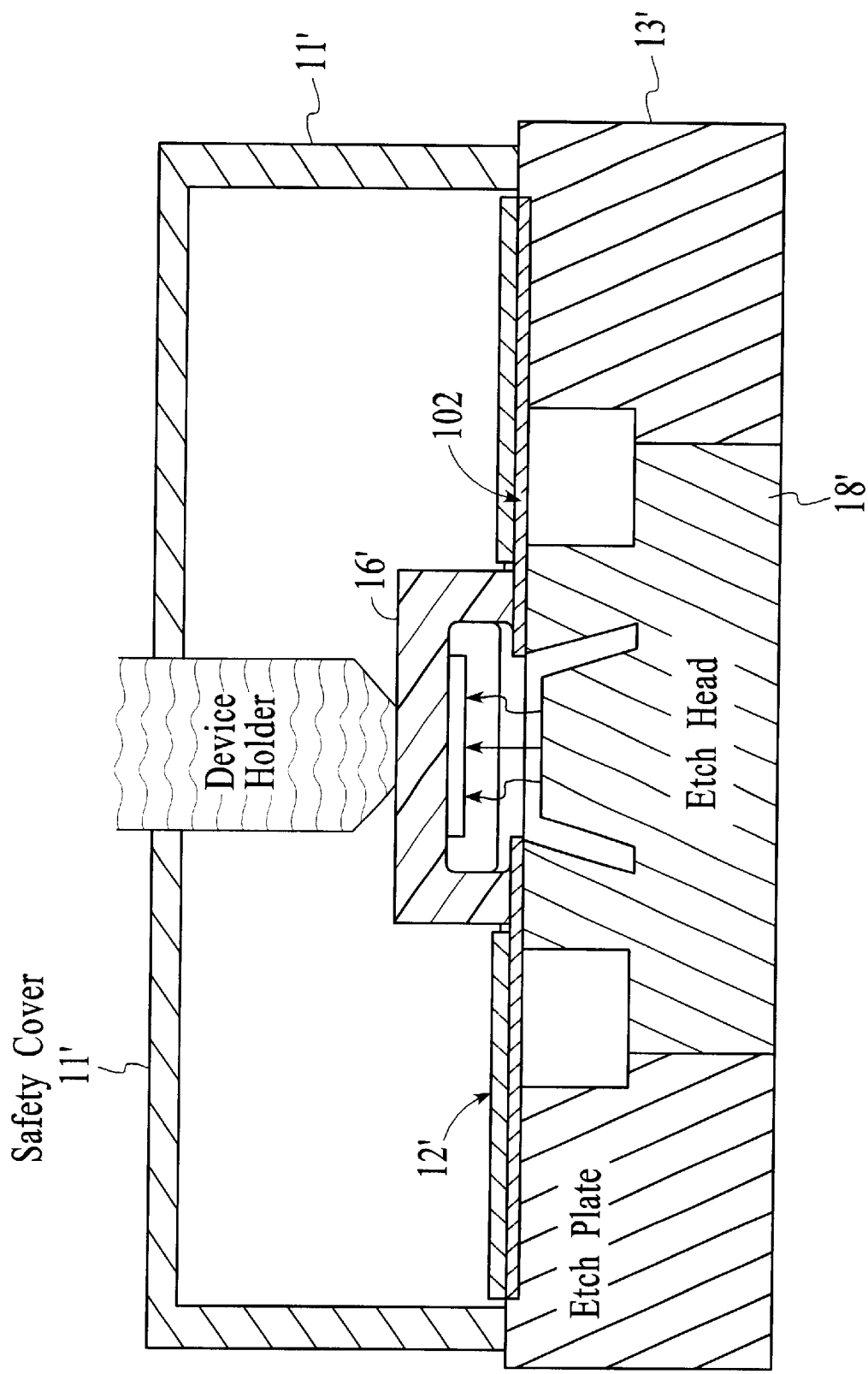
FIG. 2a illustrates a side view of the decapsulation system in accordance with the copending application.

FIG. 2a illustrates a side view of the decapsulation system 100 in accordance with the above-referenced co-pending application. The TEFLON sheet 102 replaces the gasket 14 (FIGS. 1a and 1b) utilized in the conventional automatic decapsulation system 10. The fixture 12' is still placed on top of the TEFLON sheet 102 for package alignment. FIG. 2b illustrates a top view of the system 100 in accordance wit the co-padding application. As is seen, the sheet 102 is provided with an appropriate window 104.

The system 100 allows precise decapsulation of a device by utilizing the acid resistant, high heat endurance and flexible sheet 102 as a gasket. The etch window 104 does not deform when the device 16' presses down upon the sheet 102. Thus, a precise and accurate etch is performed. Moreover, the sheet does not deteriorate with repeated decapsulation. Therefore, the device and the etch head remains clean.

Although the above-described system in the co-pending patent application functions for its intended purpose, one of ordinary skill in the art will readily recognize that it would be desirable to improve the quality of the se between the device, sheet ad the etch heads A system and method in accordance with the present invention accomplishes just that by optimizing the properties of an acid resistant, high heat endurance, and durable sheet and a rubber gasket (high compressibility). In a preferred embodiment, the sealing system in accordance with The present invention is a TEFLON sheet combined with a traditional rubber gasket. The TEFLON sheet provides a well-defined etch window for precise decapsulation, while the rubber gasket provides a tight seal between the device and etch head.

Figure 3:
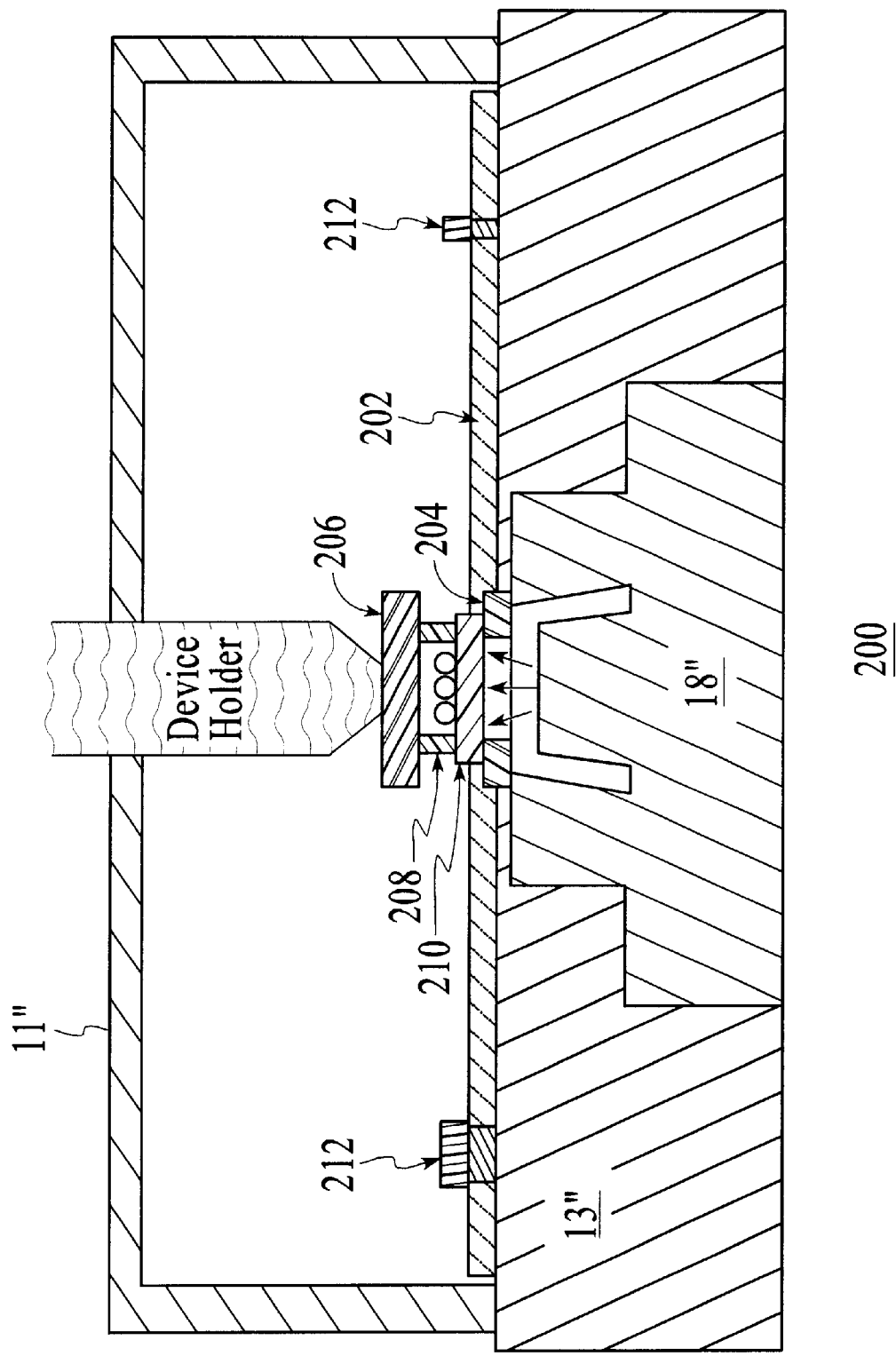
FIG. 3 is a side view of the decapsulation system in accordance with the present invention.

FIG. 3 illustrates a side view of the decapsulation system 200 in accordance with the present invention. The system 200 is similar to the systems 10 and 100 of FIGS. 1a and 2a respectively, and includes a safety cover 11" which is coupled to an etch plate 13". As is seen, a sheet 202 coupled with a rubber gasket 204 replaces the gasket 14 and positioning fixture 12 utilized in the conventional automatic decapsulation system 10 (FIG. 1a).

Figure 4A:
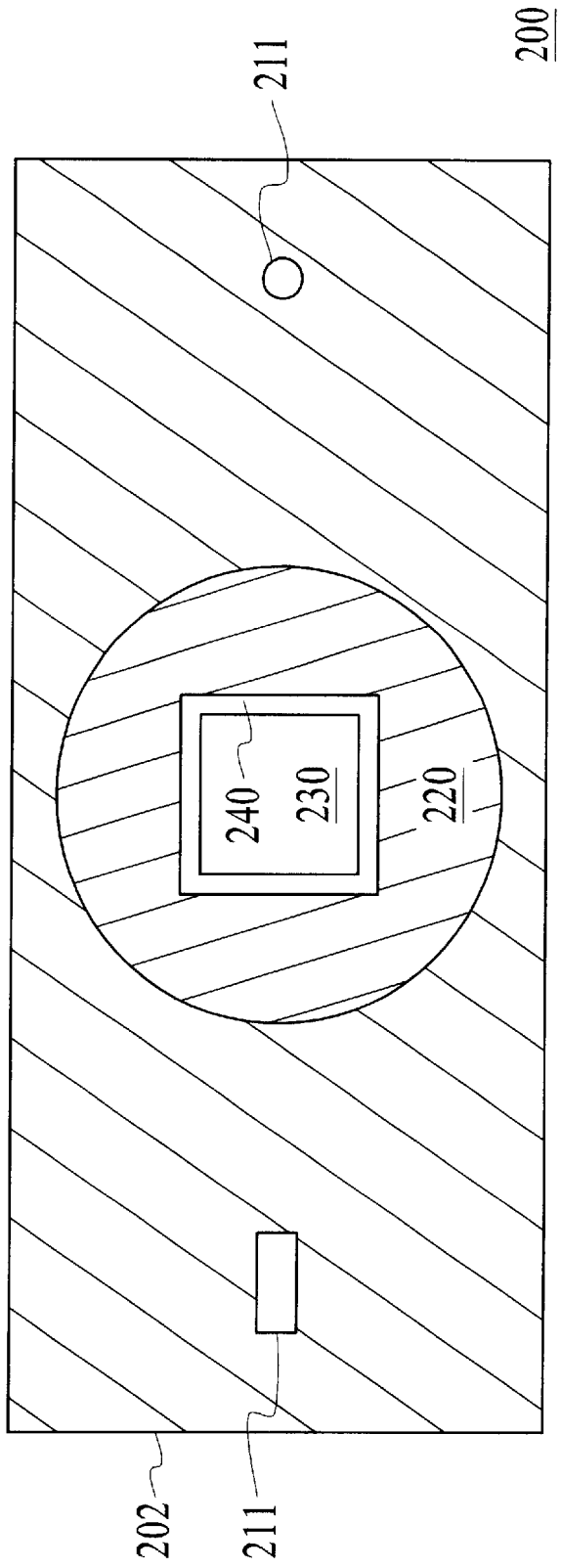
FIG. 4a illustrates a top view of the sheet in accordance with the present invention.
Figure 4B:
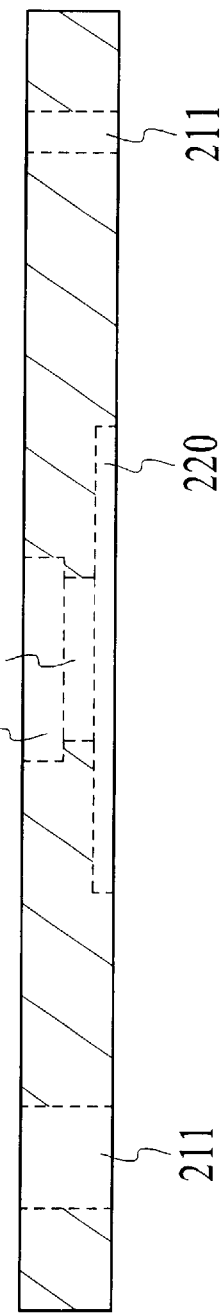
FIG. 4b illustrates a side view of the sheet in accordance with the present invention.

FIGS. 4a and 4b illustrate the top and side views, respectively, of the sheet in accordance with the present invention. The thickness of the sheet can range from 0.0625 inches to 0.125 inches to minimize etch time while maintaining etch quality. The top surface of the sheet is machined to form a first trench 240 substantially the same size as the device package 210 (FIG. 3) so that the package 210 sits in the trench 240. The bottom surface of the sheet is machined to form a second trench 220 substantially the same size as the rubber gasket 204 (FIG. 3), such that the rubber gasket 204 fits in the trench 220. The first 240 and second 220 trenches are joined by a middle opening 230 which serves as the etch window. The size of the etch window 230 is preferably substantially the same size as the integrated circuit ("IC") device within the device package 210. The rubber gasket 204 has a corresponding etch window in its center as tie sheet 202. As seen in FIG. 4a (top view), the sheet 202 has two holes 211 on both sides of the etch window 230 for fixture pins 212 (FIG. 3), which align the sheet 202 to the etch head 18" on an auto decapsulator.

Referring again to FIG. 3, the rubber gasket 204 is placed inside the sheet's 202 second trench 220 (FIG. 4b) and rotated such that the rubber gasket 204 etch window is aligned with the sheet 202 etch window. In a preferred embodiment of the present invention, the rubber gasket etch window is substantially the same shape and size as the sheet etch window, thus, alignment is simple. It is important to note, however, that the rubber gasket window opening can be larger than the sheet etch window because the etching area is sufficiently defined by the sheet etch window. The sheet 202 and rubber gasket 204 are positioned on the etch plate 13" by the fixture pins 212, wherein the etch window is automatically aligned above the etch head 18". The rubber gasket 204 sits on the etch head 18" and forms a secure seal between the etch head 18", the sheet 202, and the device 210. As is seen, the device 210 sits directly in the sheet's first trench 240 with the IC devices facing the etch head 18". Thus, the IC devices are automatically aligned with the etch window, which in turn, is aligned above the etch head 18". The device 210 preferably protrudes above the sheet's 202 surface so that the device 210 is easily removed after decapsulation.

Figure 5:
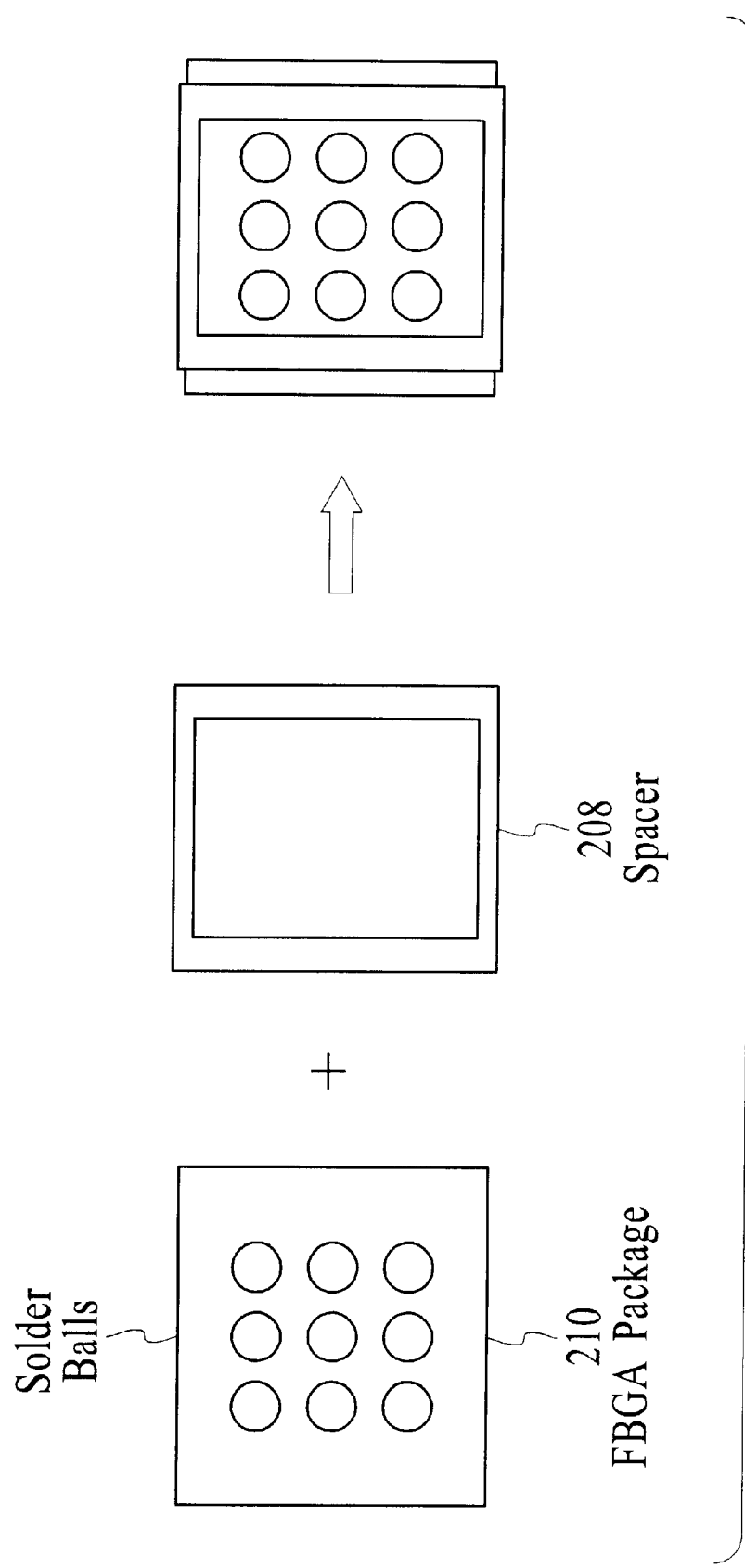
FIG. 5 is a top view of the backside of the device and spacer in accordance with the first embodiment of the present invention.

A preferred embodiment in accordance with tie present invention protects the backside of a PBGA or FBGA package 210. During high temperature decapsulation, the solder balls on a FBGA device, which are located on the backside of the device package 210, reach their melting temperature and are vulnerable to damage from the protection plate 206. A spacer 208 is inserted between the backside of the package 210 and the protection plate 206. The spacer 208 is preferably made of a TEFLON sheet having a thickness at least the height of the solder balls. FIG. 5 illustrates a top view of the backside of the device 210 with the spacer 208 in accordance with the present embodiment. As is shown, a window is cut out of the sheet 208 to surround and protect the solder balls. Accordingly, when the protection plate 206 is placed on top of The spacer 208, it does not come in contact with the backside of the device 210, and the solder balls are protected from being crushed.

As mentioned above, the present invention capitalizes on the attributes of the TEFLON sheet and the rubber gasket. TEFLON is widely used in the lab environment and other chemical/acid environments. It has features of acid resistance, high heat endurance and some flexibility (sheet material). The sheet is easily machined and relatively inexpensive. Because of the sheet's rigidity, the etch window can be made with high precision, thereby improving the accuracy and efficiency of the decapsulation. The etch window retains its shape when squeezed between the device and the etch head because TEFLON is less compressible than rubber. In addition, the sheet is durable and maintains its integrity after several etching cycles.

In turn, the rubber gasket provides a very good seal between the device, sheet, and etch head. Because the sheet separates the rubber gasket from the device, the package will not corrode. In addition, the TEFLON/rubber gasket of the first preferred embodiment produces precise package decapsulation necessary for small FBGA packages, while protecting the PCB substrate and solder balls on the package backside.

In addition to improving the decapsulation quality, the TEFLON/rubber gasket disclosed herein decreases processing time. Because of the sheet's trenches, the device package is automatically aligned with the etch window. Alignment of the etch window over the etch head is equally simple because the sheet serves as its own positioning fixture. Accordingly, high quality package decapsulation can be performed repeatedly in a shorter time period, as compared to conventional systems.

A decapsulation system in accordance with the present invention utilizes a sealing system comprising an acid resistant and high heat endurance sheet coupled with a rubber gasket to provide a seal between the device and the etch head. The sheet provides a precise etch window so that small packages, such as FBGAs, can be decapsulated without over etching and acid overflow. The sheets are easily manufactured, and are very inexpensive.

Although the present invention has been described in accordance with the embodiments shown, one of ordinary skill in the art will readily recognize that there could be variations to the embodiments and those variations would be within the spirit and scope of the present invention. For the rubber gasket's etch window can be enlarged such that the rubber gasket is substantially protected from the etchant. Accordingly, many modifications may be made by one of ordinary skill in the art without departing from the spirit and scope of the appended claims.

What is claimed is:

1. An automatic decapsulation system for a device comprising:
    an etch plate;
    an etch head for providing an etchant;
    a sheet coupled to the etch plate for providing a gasket for the device and for aligning the gasket, wherein the sheet includes a top surface and a bottom surface, wherein a first trench is provided on the top surface for receiving the device, the first trench being substantially the same size as the device and wherein the sheet is acid resistant, high heat tolerant and flexible; and
    a rubber gasket disposed between the sheet and the etch head for providing a seal between the device and the etch head.

2. The automatic decapsulation system of claim 1 in which a second trench is provided on the sheet's bottom surface for receiving the rubber gasket, the second trench being substantially the same size as the rubber gasket; and wherein the second trench is located directly below the first trench.

3. The automatic decapsulation system of claim 2 which the sheet includes a first etch window for receiving the etchant, the first etch window disposed between the first and trenches.

4. The automatic decapsulation system of claim 3 which the rubber gasket includes a second etch window for receiving the etchant.

5. The automatic decapsulation system of claim 4, wherein the second etch window in the rubber gasket is substantially the same size as the first etch window in the sheet.

6. The automatic decapsulation system of claim 3 in which the first trench, the second trench, and the first etch window are machined.

7. The automatic decapsulation system of claim 1 which includes a safety cover coupled to the etch plate.

8. The automatic decapsulation system of claim 1 wherein the sheet comprises a PFTE sheet, the PFTE sheet having a thickness that minimizes etching time.

9. The automatic decapsulation system of claim 8 wherein the PFTE sheet thickness is between 0.0625 inches to 0.125 inches.

10. An automatic decapsulation system for a device having a front side and a backside, wherein the front side contains integrated circuit devices and the backside contains solder balls, the system comprising:
    an etch plate;
    an etch head for providing an etchant;
    a PFTE sheet coupled to the etch plate for providing a gasket for the device and for aligning the gasket the PFTE sheet including a top surface and a bottom surface, wherein a first trench is provided into the top surface for receiving the front side of the device, the first trench being substantially the same size as the device;
    a rubber gasket disposed between the sheet and the etch plate for providing a seal between the device and the etch head; and
    a device securing unit for securing the device without damaging the backside of the device.

11. The automatic decapsulation system of claim 18 which a second trench is provided into the PFTE sheet's bottom surface for receiving the rubber gasket, the second trench being substantially the same size as the rubber gasket; and
    wherein the second trench is located directly below the first trench.

12. The automatic decapsulation system of claim 11 in which the PFTE sheet includes a first etch window for receiving the etchant, the first etch window disposed between the first and second trenches.

13. The automatic decapsulation system of claim 12 in which the rubber gasket includes a second etch window for receiving the etchant.

14. The automatic decapsulation system of claim 13 which the second etch window is substantially the same size as the first etch window.

15. The automatic decapsulation system of claim 10 in which the thickness of the PFTE sheet is between 0.0625 inches to 0.125 inches.

16. The system of claim 10 which the device securing unit comprises:
   a protection plate;
   a holder coupled to the protection plate for securing the device to the etch head; and
   a spacer disposed between the protection plate and the backside of the device.

17. The system of claim 16 wherein the spacer comprises:
   a PFTE sheet having a thickness of at least the height of the solder balls on the backside of the device, wherein the sheet is cut to provide a window for the solder balls, such that the sheet surrounds the backside of the device without contacting the region containing the solder balls.

18. The system of claim 16 wherein the protection plate rests on top of the spacer and the holder applies pressure on the protection plate to secure the device and to create a seal between the device, the sheet, the rubber gasket, and the etch head.

19. The automatic decapsulation system of claim 10 which includes a safety cover coupled to the etch plate.

* * * * *